(12) United States Patent
Ohtsuka

(10) Patent No.: US 8,456,158 B2
(45) Date of Patent: Jun. 4, 2013

(54) DETECTING METHOD AND DIELECTRIC PARTICLES CONTAINING MAGNETIC MATERIAL EMPLOYED IN THE DETECTING METHOD

(75) Inventor: Hisashi Ohtsuka, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 295 days.

(21) Appl. No.: 12/845,260

(22) Filed: Jul. 28, 2010

(65) Prior Publication Data

US 2011/0025315 A1 Feb. 3, 2011

(30) Foreign Application Priority Data

Jul. 31, 2009 (JP) ................................. 2009-179316

(51) Int. Cl.
*G01N 27/84* (2006.01)

(52) U.S. Cl.
USPC ........ 324/214; 435/7.92; 435/7.93; 435/7.94; 436/518; 436/526; 436/533; 436/534

(58) Field of Classification Search
USPC ............................ 324/214, 200, 250, 750.23
See application file for complete search history.

(56) References Cited

U.S. PATENT DOCUMENTS

| | | | |
|---|---|---|---|
| 6,194,223 B1 | 2/2001 | Herrmann et al. | |
| 6,376,195 B1* | 4/2002 | Mapes | 435/7.1 |
| 6,541,213 B1* | 4/2003 | Weigl et al. | 435/7.1 |
| 6,787,349 B1* | 9/2004 | Yamamoto et al. | 435/287.2 |
| 2002/0164659 A1* | 11/2002 | Rao et al. | 435/7.5 |
| 2004/0043512 A1 | 3/2004 | Song et al. | |
| 2004/0126904 A1 | 7/2004 | Watkins et al. | |
| 2005/0053974 A1 | 3/2005 | Lakowicz et al. | |
| 2006/0130192 A1 | 6/2006 | Lee et al. | |
| 2007/0020699 A1 | 1/2007 | Carpenter et al. | |
| 2007/0020700 A1 | 1/2007 | Carpenter et al. | |

(Continued)

FOREIGN PATENT DOCUMENTS

| | | |
|---|---|---|
| EP | 2110658 A1 | 10/2009 |
| JP | 01-272970 A | 10/1989 |

(Continued)

OTHER PUBLICATIONS

Ekgasit, S., Fluorescence intensity in surface-plasmon field-enhanced fluorescence spectroscopy, Elsevier, May 24, 2004, p. 295-301.*

(Continued)

*Primary Examiner* — Huy Q Phan
*Assistant Examiner* — Giovanni Astacio-Oquendo
(74) *Attorney, Agent, or Firm* — Sughrue Mion, PLLC

(57) ABSTRACT

A magnetic binding substance, which is a first binding substance that specifically binds with a target substance, having magnet enveloping dielectric particles, which have magnetic particles enveloped therein and surfaces modified with functional groups that exhibit polarity within a liquid sample, attached thereto, and a labeling binding substance, which is a second binding substance that specifically binds with the target substance having photoresponsive labels attached thereto, are mixed with the liquid sample such that binding reactions occur. A magnetic field is generated within a sample cell, to draw the magnetic binding substance to a local region. Excitation light is irradiated only onto a predetermined region including the local region while the magnetic binding substance is drawn to the local region, causing the photoresponsive labels present therein to generate optical signals. The optical signals are detected.

18 Claims, 7 Drawing Sheets

U.S. PATENT DOCUMENTS

| | | | |
|---|---|---|---|
| 2007/0105163 | A1* | 5/2007 | Grate et al. .................. 435/7.5 |
| 2009/0110642 | A1 | 4/2009 | Woo et al. |
| 2009/0142772 | A1 | 6/2009 | Lau et al. |
| 2009/0261269 | A1 | 10/2009 | Horii et al. |
| 2009/0321662 | A1 | 12/2009 | Ohtsuka |
| 2010/0092996 | A1 | 4/2010 | Verschuren et al. |

FOREIGN PATENT DOCUMENTS

| | | |
|---|---|---|
| JP | 05-264547 A | 10/1993 |
| JP | 2001021565 A | 1/2001 |
| JP | 2005-077338 A | 3/2005 |
| JP | 2006292721 A | 10/2006 |
| JP | 2007-045982 A | 2/2007 |
| JP | 2007071811 A | 3/2007 |
| JP | 2008249361 A | 10/2008 |
| JP | 2008309514 A | 12/2008 |
| JP | 2009080006 A | 4/2009 |
| WO | 2007/011936 A2 | 1/2007 |
| WO | 2007/053181 A2 | 5/2007 |
| WO | 2008/072156 A2 | 6/2008 |
| WO | 2009/009408 A2 | 1/2009 |
| WO | 2009/069009 A1 | 6/2009 |

OTHER PUBLICATIONS

Schmidt B., Optofluidic trapping and transport on solid core waveguides within a microfluidic device, Optic Express, Sep. 27, 2007, p. 14322-14334.*

The Gale Group, Inc., The Great Soviet Encyclopedia, 3rd Edition, (1970-1979), http://encyclopedia2.thefreedictionary.com/Chemiluminescence.*

Communication Pursuant to Article 94(e) EPC; Application No. 10 171 059.8-2401; Jan. 23, 2012.

Extended European Search Report relating to Application No. 10171059.8, dated Jan. 23, 2012.

Extended European Search Report relating to European Patent Application No. 10171059.8, dated Nov. 22, 2010.

Margarida M. L. M. Vareiro, et al., "Surface Plasmon Fluorescence Measurements of Human Chorionic Gonadotrophin: Role of Antibody Orientation in Obtaining Enhanced Sensitivity and Limit of Detection", Analytical Chemistry, Apr. 2005, pp. 2426-2431, vol. 77, No. 8.

K. Tsuboi, et al., "High-sensitivity sensing of catechol amines using by optical waveguide mode enhanced fluorescence spectroscopy", Abstracts of the Spring 2007 Conference of the Academy of Applied Physics, 2007, p. 1378, No. 3, 28p-SA-4.

T. Liebermann, et al., "Surface-plasmon field-enhanced fluorescence spectroscopy", Colloids and Surfaces A, 2000, pp. 115-130, vol. 171.

Gang Xie, et al., "Preparation and Characterization of Monodisperse Magnetic Poly(styrene butyl acrylate methacrylic acid) Microspheres in the Presence of a Polar Solvent", Journal of Applied Polymer Science, 2003, pp. 1733-1738, vol. 87.

Mikio Hikata, et al., "Manufacture of Polystyrene Standard Particles and Their Applications", Aerosol Research, 2007, pp. 282-288, vol. 22, No. 4.

A. Narita, et al., "Functionalization of Inorganic Nanoparticles with Organic Molecules", Papers Regarding Polymer Molecules, May 2008, pp. 321-333, vol. 65, No. 5.

D. Maity, et al., "Synthesis of iron oxide nanoparticles under oxidizing environment and their stabilization in aqueous and non-aqueous media", Journal of Magnetism and Magnetic Materials, 2007, pp. 46-55, vol. 308.

Japanese Office Action Patent Application No. 2009-179316; Nov. 20, 2012 with partial English translation.

* cited by examiner

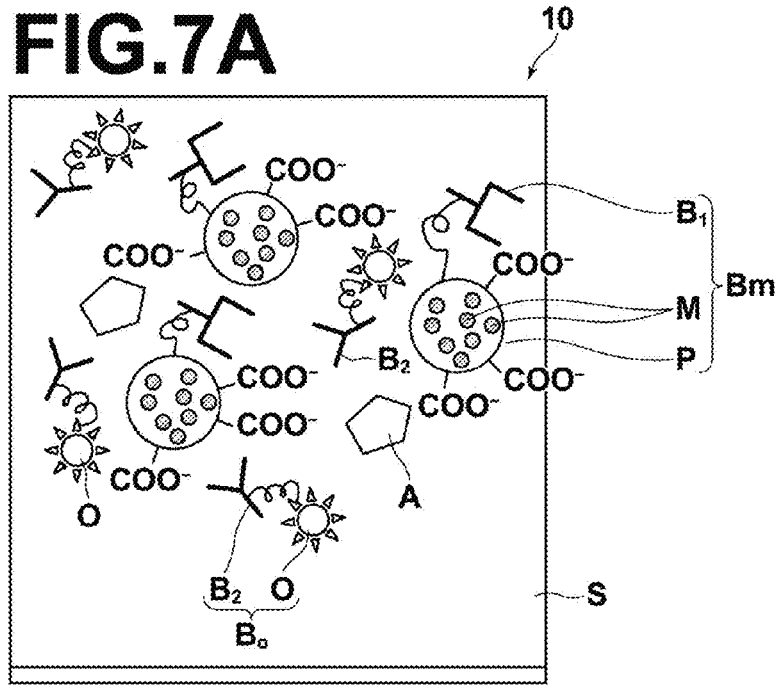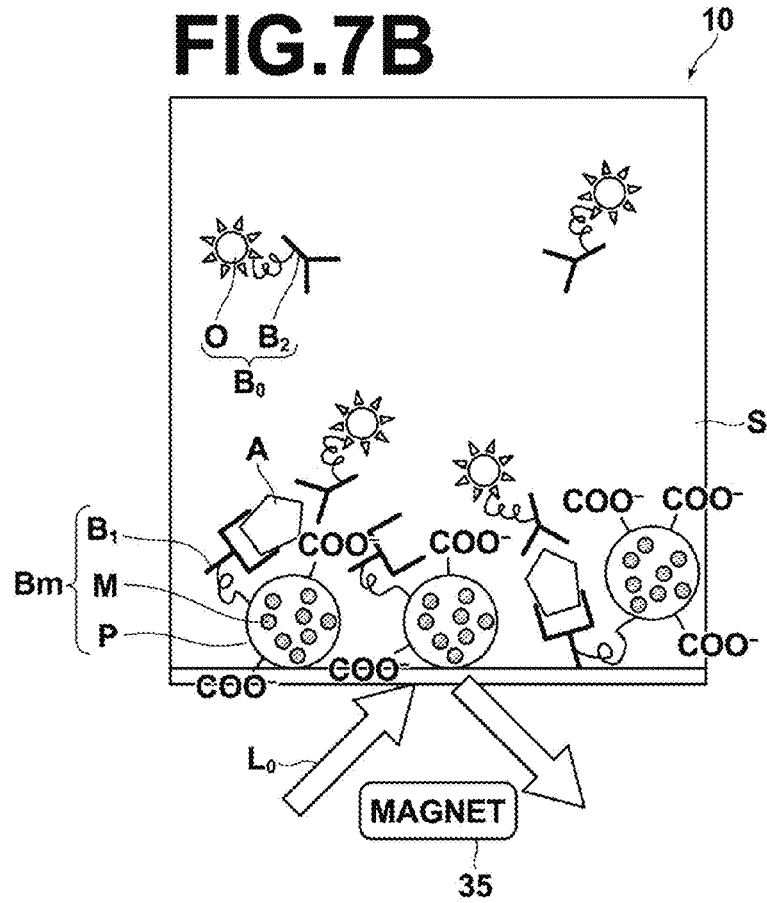

DETECTING METHOD AND DIELECTRIC PARTICLES CONTAINING MAGNETIC MATERIAL EMPLOYED IN THE DETECTING METHOD

BACKGROUND OF THE INVENTION

1. Field of the Invention

The present invention is related to a detecting method for detecting detection target substances within samples. The present invention is also related to magnet enveloping dielectric particles which are employed in the detecting method.

2. Description of the Related Art

Assay methods such as the sandwich method and the competition method are well known in the field of biological measurement. In the sandwich method, primary antibodies that specifically bind to antigens, which are detection target substances included in a sample, are immobilized onto the surface of a substrate. The sample is supplied onto the substrate, to cause the detection target substances to specifically bind to the primary antibodies. Next, secondary antibodies that specifically bind to the antigens and which have fluorescent labels attached thereto are caused to bind with the antigens, thereby forming so called sandwiches constituted by the primary antibodies, the antigens, and the secondary antibodies. Thereafter, fluorescence emitted by the fluorescent labels which are attached to the secondary antibodies is detected.

Evanescent fluorometry, in which fluorescence labels are excited by evanescent light, has been proposed as a method for detecting fluorescence emitted by fluorescent labels. In evanescent fluorometry, an excitation light beam is caused to enter a surface from the rear surface thereof and to be totally reflected at the front surface of the substrate. Fluorescent labels are excited by evanescent light that leaks onto the front surface of the substrate. Thereafter, fluorescence emitted by the fluorescent labels is detected.

Meanwhile, a method that utilizes the electric field enhancing effect of plasmon resonance in order to improve the sensitivity of evanescent fluorometry has been proposed in U.S. Pat. No. 6,194,223 and "Surface Plasmon Fluorescence Measurements of Human Chorionic Gonadotrophin: Role of Antibody Orientation in Obtaining Enhanced Sensitivity and Limit of Detection", M. M. L. M. Vareiro et al., Analytical Chemistry, Vol. 77, No. 3, pp. 2426-2431, 2005. In this surface plasmon enhanced fluorometry method, a metal layer is provided on a substrate, and excitation light is caused to enter the interface between the substrate and the metal layer at an incident angle greater than or equal to a total reflection angle. Surface plasmon is generated at the metal layer by the excitation light, and fluorescence signals are amplified by the electric field enhancing effects of the surface plasmon, to improve the S/N ratio.

In addition, a method in which the electric field enhancing effects of an optical waveguide mode is utilized in order to enhance the electric field at the sensor portion, similarly to the surface plasmon enhanced fluorometry method, has been proposed in "High-sensitivity sensing of catechol amines using by optical waveguide mode enhanced fluorescence spectroscopy", K. Tsuboi et al., Abstracts of the Spring 2007 Conference of the Academy of Applied Physics, No. 3, p. 1378, 28p-SA-4, 2007. In optical waveguide mode enhanced fluorescence spectroscopy, a metal layer and an optical waveguide layer constituted by a dielectric or the like are sequentially provided on a sensor portion. An optical waveguide mode is generated in the optical waveguide layer, and fluorescence signals are amplified by the electric field enhancing effects thereof.

In addition, U.S. Patent Application Publication No. 20050053974 and "Surface-plasmon field-enhanced fluorescence spectroscopy", T. Liebermann and W. Knoll, Colloids and Surfaces A, Vol. 171, pp. 115-130, 2000, propose methods for detecting radiant light (SPCE: Surface Plasmon Coupled Emission), which is generated by surface plasmon induced at metal layers by fluorescence generated by fluorescent labels, instead of detecting fluorescence emitted by fluorescent labels and amplified by surface plasmon, as in the aforementioned fluorometry methods.

As described above, various methods for detecting detection target substances, which are labeled with fluorescent labels, have been proposed in the field of biological measurement.

Meanwhile, in cases that fluorescence is detected after forming sandwiches with primary antibodies which are immobilized onto substrates as described above, it is necessary to separate the sandwich combinations and secondary antibodies that have not undergone binding reactions with the detection target substance. Therefore, cleansing operations to wash away such non reactive secondary antibodies is necessary to perform measurements. Not only are the cleansing operations troublesome, but they are also a factor in increasing the amount of time required for measurements. In addition, there are cases that a portion of the detection target substance will be discarded along with supernatant liquid during the cleansing operation. Therefore, there is a possibility that the detection sensitivity will deteriorate in cases that the detection target substance is a trace component within a sample. In addition, the reaction between the detection target substance and the primary antibodies is a reaction between a solid phase surface, on which the primary antibodies are bound, and a solution (liquid phase) that includes the detection target substance. Therefore, the reaction efficiency is poor, which is another factor that prevents expedient measurements.

In this respect, Japanese Unexamined Patent Publication No. 2005-077338 proposes a method that realizes high speed measurements, does not require a cleansing operation, is capable of quantifying detection target substances, and further solves the problem of delayed reactions between the solid phase and liquid phase. Specifically, in this method, primary antibodies are labeled with magnetic particles, secondary antibodies are labeled with fluorescent pigment, combinations of the primary antibodies, the detection target substance, and the secondary antibodies are formed within the liquid phase without immobilizing the primary antibodies onto a substrate. The combinations are localized by magnets, to separate them from non reactive secondary antibodies, and evanescent light is irradiated onto the localized combinations to measure fluorescent signals, without undertaking a cleansing operation.

Note that paragraph [0030] of Japanese Unexamined Patent Publication No. 2005-077338 describes that it is preferable for the particle size of the magnetic particles to be 100 nm (0.1 µm) or less, from the viewpoint of dispersion properties within liquid samples, that is, in order to prevent agglomeration of the particles with each other.

Similarly, Japanese Unexamined Patent Publication No. 5(1993)-264547 proposes a sensing method that employs magnetic particles. An example is described in which fine particles having particle sizes of 100 nm or less are employed as the magnetic particles.

However, in experiments that we have conducted, expedient localization (concentration) of combinations could not be reproduced using magnetic particles having particle sizes of 100 nm or less. That is, concentration could not be achieved within several minutes, which is a level required for practical use.

Meanwhile, Japanese Unexamined Patent Publication No. 1(1989)-272970 discloses a method that employs magnetic particles having a particles size of several tens of nanometers. In this method, individual magnetic particles and combinations of the magnetic particles and a detection target substance are separated by the difference in the responses thereof with respect to a magnet, that is, by the difference in concentration speeds, to measure signals from the combinations.

Detecting methods that employ localization by magnetic particles are extremely attractive as biological measurement methods, because they enable reactions in the liquid phase and they obviate cleansing operations to separate combinations of substances and non reactive secondary antibodies. However, these methods have remained merely concepts, and were not put into practical use.

As a result of investigation into the reasons why such methods are not practical, the resent inventors discovered the following problems which are encountered when actually practicing localization of combinations using magnetic particles.

1) Depending on the storage conditions of the magnetic particles, there is a possibility that the magnetic particles are magnetized and agglomerate prior to use in detection, which leads to deterioration in dispersion properties during use.
2) In the case that the magnetic particles include metal materials, there is a possibility that metal quenching, a phenomenon in which optical signals are absorbed by metals, will occur when the magnetic particles come into the vicinities of photoresponsive labels. This leads to a decrease in the amount of detected optical signals, which in turn leads to deterioration (fluctuations) in the quantitative properties of the signals.

SUMMARY OF THE INVENTION

The present invention has been developed in view of the foregoing circumstances. It is an object of the present invention to provide a detecting method that utilizes localization of combinations by magnetic particles that solves the aforementioned problems and is suitable for practical use.

A detecting method of the present invention comprises the steps of:

preparing a magnetic property imparted binding substance, which is a first binding substance that specifically binds with a detection target substance, having magnet enveloping dielectric particles, which have magnetic particles enveloped therein and the surfaces of which are modified with functional groups that exhibit polarity within a liquid sample, attached thereto;

preparing a labeling binding substance, which is one of a second binding substance that specifically binds with the detection target substance and a third binding substance that specifically binds with the first binding substance in competition with the detection target substance, having photoresponsive labels attached thereto;

mixing the liquid sample, which is a target of inspection, the magnetic property imparted binding substance, and the labeling binding substance, to cause binding reactions to occur;

generating a magnetic field within a sample cell that contains the liquid sample, in which the magnetic property imparted binding substance and the labeling binding substance are mixed, to draw the magnetic property imparted binding substance to a local region within the sample cell;

irradiating excitation light only onto a predetermined region that includes the local region, in a state in which the magnetic property imparted binding substance is drawn to the local region, to cause optical signals to be generated by the photoresponsive labels which are present within the predetermined region;

detecting the optical signals; and determining the amount of the detection target substance within the liquid sample, based on the amount of detected optical signals.

Examples of the functional groups that modify the surfaces of the magnet enveloping dielectric particles include basic functional groups such as amino groups and quaternary ammonium groups, and acidic functional groups that cause the particles to be charged with negative charges, such as carboxyl groups, sulfonic acid groups, and phosphoric acid groups.

Here, in the case that an assay is performed according to the sandwich method, it is preferable for the maximum length of the combinations (the sandwich combination) of the magnetic property imparted binding substance, the detection target substance, and the labeling binding substance, which is the second binding substance having the photoresponsive labels attached thereto, to be greater than or equal to 200 nm. In the case that an assay is performed according to the competition method, it is preferable for the maximum length of the combinations (the competitive combinations) of the magnetic property imparted binding substance and the labeling binding substance, which is the third binding substance having the photoresponsive labels attached thereto, to be greater than or equal to 200 nm. Here the maximum length refers to the long diameter of the combinations, and is basically the total length of the plurality of elements which are linked together to form the combinations.

It is preferable for the particle size of the magnet enveloping dielectric particles to be within a range from 100 nm to 1 μm, and preferably to be within a range from 150 nm to 1 μm.

Resin, SiO2 particles and the like are preferred dielectrics.

A single magnetic particle or a plurality of magnetic particles may be enveloped within each dielectric particle. Any magnetic material may be employed as long as it is capable of being drawn to the local region by the magnetic field generated by a magnet or the like. Iron based magnetic materials or platinum based magnetic materials are preferred as the material of the magnetic particles. In the case that an iron based magnetic material or a platinum based magnetic material is employed for the magnetic particles, it is desirable for infrared radiation to be employed as the excitation light.

The photoresponsive labels may be those that emit fluorescence as the optical signals when irradiated by the excitation light. Alternatively, the photoresponsive labels may be those that generate scattered light as the optical signals when irradiated by the excitation light. As a further alternative, the photoresponsive labels may be those that generate local plasmon as the optical signals when irradiated by the excitation light. Specific examples of the photoresponsive labels include fluorescent pigment molecules, fine fluorescent particles having fluorescent pigment molecules enveloped within a dielectric material, and fine metal particles. The fine metal particles generate scattered light and generate local plasmon on the surfaces thereof when irradiated by the excitation light. In this case, the scattered light may be detected as the optical signals, or radiant light caused by the local plasmon may be detected as the optical signals.

A sample cell with a portion of a wall having a sample contacting surface that contacts the liquid sample, which is constituted by a transparent dielectric plate, may employed as the sample cell. In this case, the vicinity of the sample contacting surface is employed as the local region, and light is irradiated onto the sample contacting surface of the of the dielectric plate from outside the wall constituted by the dielectric plate under conditions of total reflection, such that evanescent light is generated at the sample contacting surface, and the evanescent light may be employed as the excitation light.

A sample cell, in which a metal film is formed on the sample contacting surface of the dielectric plate, maybe employed as the sample cell. In addition, a sample cell, which is further equipped with an optical waveguide layer provided on the metal film, may be employed as the sample cell.

The optical signals may be either directly detected or indirectly detected.

In the case that the sample cell equipped with the dielectric plate having the metal film formed thereon is employed, detecting radiant light that radiates due to excitation of surface plasmon at the metal film by the optical signals is a favorable method for indirectly detecting the optical signals generated by the photoresponsive labels due to the irradiation of the excitation light. In the case that the sample cell equipped with the metal film having the optical waveguide layer formed thereon is employed, detecting radiant light that radiates due to excitation of an optical waveguide mode of the optical waveguide layer by the optical signals is a favorable method for indirectly detecting the optical signals generated by the photoresponsive labels due to the irradiation of the excitation light.

In the case that the photoresponsive labels are those that generate fluorescence, the fluorescence excites surface plasmon on the metal layer, or an optical waveguide mode in the optical waveguide layer. On the other hand, in the case that the photoresponsive labels are fine metal particles, the local plasmon which is generated on the surfaces of the fine metal particles by the excitation light functions as the optical signals that excite surface plasmon on the metal layer, or an optical waveguide mode in the optical waveguide layer.

Magnet enveloping dielectric particles of the present invention comprise:

magnetic particles enveloped therein; and functional groups that exhibit polarity within liquid samples, provided as surface modifications.

It is preferable for the functional groups to be carboxyl groups. In addition, it is preferable for the magnetic particles to be formed by either an iron based magnetic material or a platinum based magnetic material.

The detecting method of the present invention employs the magnet enveloping dielectric particles having the magnetic particles enveloped within dielectrics, the surfaces of which are modified with the functional groups that exhibit polarity within liquid samples. Therefore, even if the magnetic particles within the dielectric particles are magnetized and the dielectric particles agglomerate during storage, the polarities of the functional groups on the surfaces thereof will cause them to repel each other within liquid samples, to improve the dispersion properties thereof. In addition, because the magnetic particles are enveloped within the dielectrics, the magnetic particles and the photoresponsive labels can be separated to a degree. Accordingly, metal quenching can be suppressed in the case that the magnetic particles are formed by metal materials, to suppress decreases in signal intensity and fluctuations in signal amounts. Further, the organic substances can be more easily provided as surface modifications to dielectric particles compared to cases in which the surfaces of magnetic particles are modified. Therefore, providing the functional groups as surface modifications and attachment of the dielectric particles to the first binding substance can be easily performed, regardless of the material of the magnetic particles.

The maximum length of the sandwich combinations may be 200 nm or greater in the case that assays are performed according to the sandwich method. The maximum length of the competitive combinations may be 200 nm or greater in the case that assays are performed according to the competition method. In these cases, the agglomerating properties are improved, and the amount of time required for measurement can be shortened to a practical level (several minutes).

Further, the particle size of the magnet enveloping dielectric particles may be 100 nm or greater. In this case, the size of the combinations can easily become 200 nm or greater, and accordingly, the agglomerating properties are improved, and the amount of time required for measurement can be shortened to a practical level (several minutes).

As described in the section "Description of the Related Art", in the experiments conducted by the present inventors, there was a problem that the disturbance imparted by Brownian motion led to slow concentration speeds, which resulted in too much time elapsing before an amount of agglomeration sufficient to enable measurements. On the other hand, as described in Japanese Unexamined Patent Publication No. 2005-077338 that it is preferable for the particle size of the magnetic particles to be 100 nm or less, there is a problem that dispersion properties deteriorate in cases that the particle size exceeds 100 nm. That is, it was extremely difficult to achieve both dispersion and agglomeration (obtainment of magnetic force that overcomes Brownian motion) of the magnetic particles. In this respect, the present invention employs the magnet enveloping dielectric particles having the functional groups that exhibit polarity within liquid samples on the surfaces thereof. Thereby, the dispersion properties within the liquid samples are secured, while the agglomeration properties are improved by setting the maximum length of the combinations to 200 nm or greater and the particle sizes of the magnet enveloping dielectric particles to be within a range from 100 nm to 1 μm. That is, the present invention improves suitability for practical use, by achieving both dispersion properties and agglomeration properties.

BRIEF DESCRIPTION OF THE DRAWINGS

FIG. 7A is a diagram that illustrates the steps of the detecting method according to the first embodiment of the present invention (prior to magnetic field application).

FIG. 7B is a diagram that illustrates the steps of the detecting method according to the first embodiment of the present invention (following magnetic field application).

DESCRIPTION OF THE PREFERRED EMBODIMENTS

Figure 1:
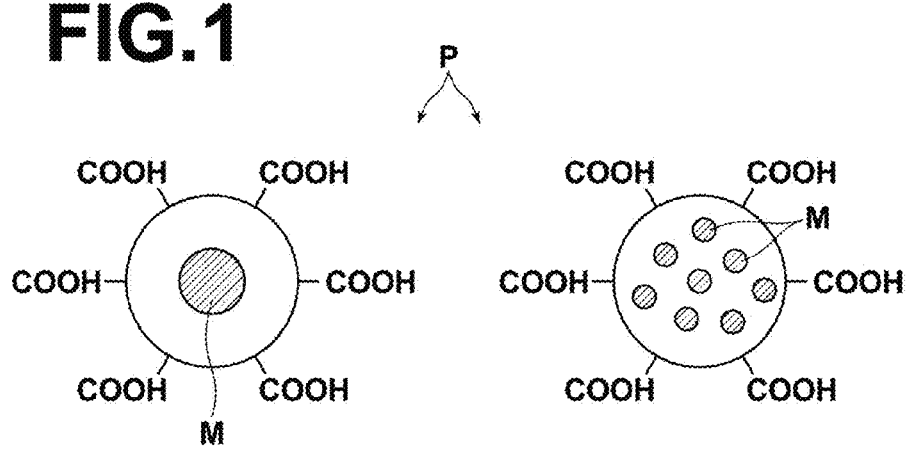
FIG. 1 is a schematic diagram that illustrates the configurations of magnet enveloping dielectric particles.

Hereinafter, embodiments of the present invention will be described with reference to the attached drawings. Note that the dimensions of the constituent parts illustrated in the drawings differ from the actual dimensions thereof, in order to facilitate descriptions thereof.

[Magnet Enveloping Dielectric Particles]

First, the magnet enveloping dielectric particles P which are employed in the detecting method of the present invention will be described. As illustrated in FIG. 1A and FIG. 1B, the magnet enveloping dielectric particles P have one or a plurality of magnetic particles M enveloped therein, as well as functional groups that exhibit polarity within liquid samples provided as surface modifications.

The shape of the magnetic particles M is not particularly limited, and examples of possible shapes include spheres and rods. However, it is preferable for the particle size thereof to be 100 nm or less, and it is favorable for the particle size thereof to be within a range from 15 nm to 40 nm in the case that a plurality of magnetic particles M are enveloped in the magnet enveloping dielectric particles P. The material of the magnetic particles M is not particularly limited, and examples of the material of the magnetic particles M include: ferrosoferic oxide; iron sesquioxide; various ferrites; metals such as iron, manganese, nickel, cobalt, chrome, and platinum; and alloys of the aforementioned metals. Iron based magnetic materials such as iron oxide and platinum based magnetic materials such as alloys that include platinum are particularly preferable.

Examples of the dielectric material include resin materials and $SiO_2$. Examples of the resin materials include: polystyrene; polymethyl methacrylate (PMMA); and latex, in which bridging materials (reagents that form bridges among polymer chains, such as divinyl benzene and 1, 4 butadiene) are polymerized together.

In the examples illustrated in FIG. 1, the functional groups are carboxyl groups, which are acidic functional groups that cause negative charges to be charged. However, any functional groups may be employed, as long as they exhibit polarity within sample liquids. Examples of other functional groups include basic functional groups such as amino groups and quaternary ammonium groups, and acidic functional groups such as sulfonic acid groups and phosphoric acid groups.

The shape of the magnet enveloping dielectric particles P is not particularly limited, and examples of possible shapes include spheres and rods. In addition, it is preferable for the particle size of the magnet enveloping dielectric particles to be within a range from 100 nm to 1 μm, and more preferably to be within a range from 150 nm to 1 μm. Note that here, the particle size refers to the maximum dimension of the particles.

Figure 2:
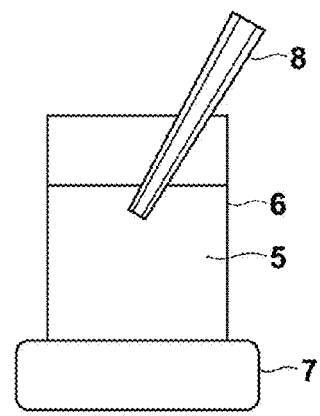
FIG. 2 is a diagram for explaining a measurement method for magnetic concentration indices.

The preferred particle size of the magnet enveloping dielectric particles P was derived by conducting the following experiment. As illustrated in FIG. 2, in the experiment, the magnet enveloping dielectric particles P were dispersed within a solution 5. Then, a magnet 7 was positioned beneath the bottom surface of a sample container 6, to perform a magnetic separation process (agglomeration). Supernatant liquid of the sample solution 5 was suctioned by a pipette 8 prior to and following the magnetic separation process. The degree of light absorbency (degree of transparency) of the suctioned supernatant liquid was measured with respect to light having a wavelength of 500 nm.

Figure 3:
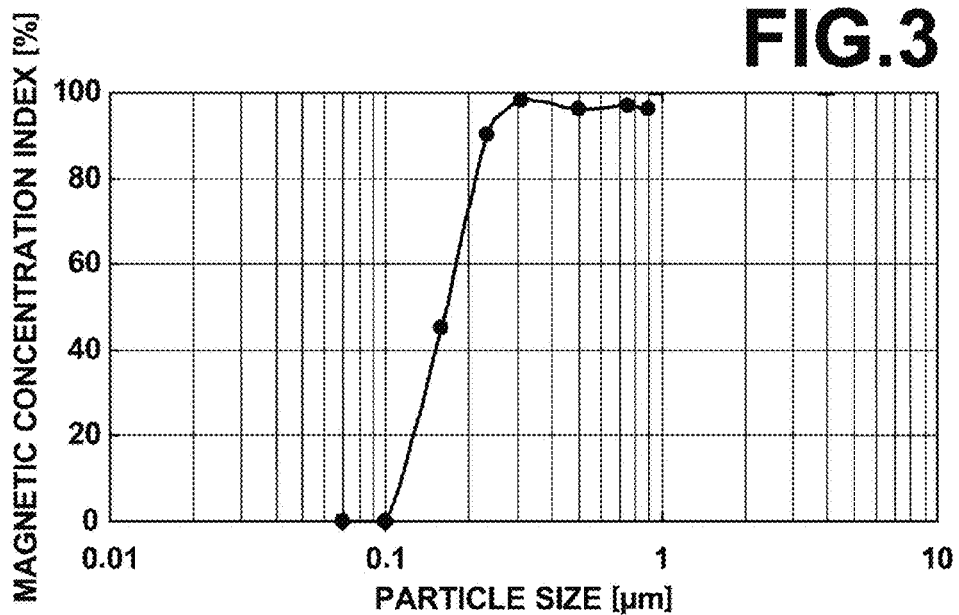
FIG. 3 is a diagram that illustrates the dependent nature of magnetic concentration indices on particle sizes.
Figure 4A:
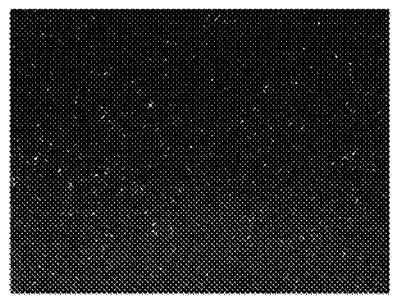
FIG. 4A is a dark field microscope photograph that illustrates the dispersion state of magnet enveloping dielectric particles prior to magnetic concentration.
Figure 4B:
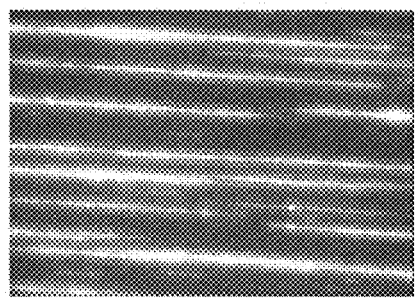
FIG. 4B is a dark field microscope photograph that illustrates the dispersion state of magnet enveloping dielectric particles during magnetic concentration.
Figure 4C:
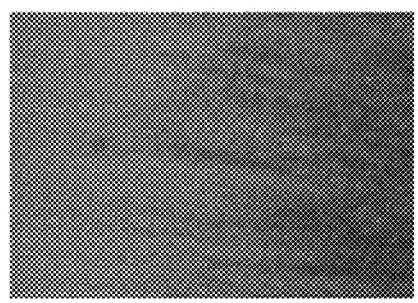
FIG. 4C is a dark field microscope photograph that illustrates the redispersed state of magnet enveloping dielectric particles following magnetic concentration.
Figure 5A:
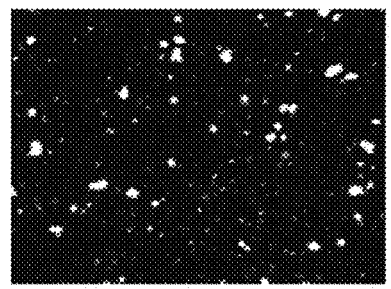
FIG. 5A is a dark field microscope photograph that illustrates the dispersion state of magnetic particles prior to magnetic concentration (comparative example).
Figure 5B:
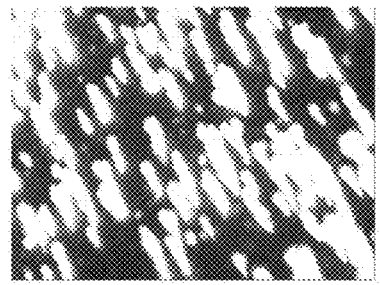
FIG. 5B is a dark field microscope photograph that illustrates the dispersion state of magnetic particles during magnetic concentration (comparative example).
Figure 5C:
FIG. 5C is a dark field microscope photograph that illustrates the redispersed state of magnetic particles following magnetic concentration (comparative example).

A degree of light absorbency A was measured one minute after the magnet was positioned, and a degree of light absorbency B was measured for the sample solution prior to the magnet being positioned, as the degrees of light absorbency following and prior to the magnetic separation process. A magnetic concentration index was calculated from the measured values by the formula: $100 \cdot (B-A)/B$ (%). The dependent nature of the agglomeration ability (magnetic concentration index) on particle size of the magnet enveloping dielectric particles P is illustrated in FIG. 3. In FIG. 3, the vertical axis represents the magnetic concentration index, and indicates that the agglomeration ability is higher (that is, the degree of transparency following the magnetic concentration process is higher) as the numerical values increase.

As illustrated in FIG. 3, in cases that the particle size is 100 nm or less, almost no agglomeration (localization) of the magnet enveloping dielectric particles P occurs after one minute of the magnetic separating process. On the other hand, the concentration index gradually increases as the particle size exceeds 100 nm. The concentration index is approximately 50% at a particle size of 150 nm, 80% at a particle size of 200 nm, and substantially 100% at a particle size of 300 nm after one minute of the magnetic separating process. That is, it became clear that agglomeration was occurring swiftly at particle sizes greater than 100 nm.

Based on the experiment results above, it is considered that a particle size of 200 nm or greater is necessary for localization to occur at a practically usable level (here, one minute). Note that it is considered that concentration speeds sufficient for practical use may be achieved by adopting particle sizes within a range from 200 nm to 1 μm. However, if the particle size becomes excessively large, there is a problem that dispersion properties will decrease. Smaller particle sizes are preferable from the viewpoint of dispersion properties. Accordingly, a particle size of 200 nm is optimal.

However, the aforementioned experiment measured the agglomeration ability of only the magnet enveloping dielectric particles P. In actuality, agglomeration is performed in a state in which sandwich combinations or competitive combinations formed by antigen antibody reactions are formed. Therefore, it is considered that the sizes (maximum length) of each of the sandwich combinations or each of the competitive combinations as a whole is 200 nm or greater. That is, concentration speeds sufficient for practical use can be achieved even if the particle size of the magnet enveloping dielectric particles is less than 200 nm, as long as the sizes of the combinations with a labeling binding substance according to the assay method are 200 nm or greater.

In the case that TF antibodies are a detection target substance, the sizes of the antibodies that constitute sandwich combinations are approximately 15 nm and several nm (up to 10 nm). In the case that the particle size of the magnet enveloping dielectric particles is 100 nm, maximum lengths of 200 nm or greater can be realized for the combinations, by employing fluorescent beads of approximately 100 nm as labels in the labeling binding substance. In the case that the particle size of the magnet enveloping dielectric particles is approximately 160 nm, maximum lengths of 200 nm or greater can be realized for the combinations, even if fluorescent pigment (up to 1 nm in size) such as cy-3 and cy-5 are employed as the labels in the labeling binding substance.

The dispersion properties of the magnet enveloping dielectric particles will be described.

FIGS. 4A through 4C are dark field microscope photographs of the states of the magnet enveloping dielectric particles employed in the present invention having a particle size of 150 nm, when they are initially dispersed into a solution (FIG. 4A), during magnetic agglomeration due to application of a magnetic field (FIG. 4B), and after application of the magnetic field is ceased (FIG. 4C).

For comparative purposes, FIGS. 5A through 5C are dark field microscope photographs of the states of the magnetic particles of the same particle size as the magnet enveloping dielectric particles, when they are initially dispersed into a solution (FIG. 5A), during magnetic agglomeration due to application of a magnetic field (FIG. 5B), and after application of the magnetic field is ceased (FIG. 5C). Note that the surfaces of the magnet enveloping dielectric particles and the magnetic particles were each modified by favorable known methods which have been disclosed in publications. That is, the surfaces of the magnet enveloping dielectric particles were modified with carboxyl groups by the method disclosed in paragraph of Japanese Unexamined Patent Publication No. 2007-045982; "Preparation and Characterization of Monodisperse Magnetic Poly(styrene butyl acrylate methacrylic acid) Microspheres in the Presence of a Polar Solvent", G. Xie et al., Journal of Applied Polymer Science, Vol. 87, pp. 1733-1738, 2003; and Chapter 3.1 "Synthesizing Particles" of "Manufacture of Polystyrene Standard Particles and Their Applications", M. Hikata et al., Aerosol Research, Vol. 22, No. 4, pp. 282-288, 2007, in which "magnetic polymer particles having carboxyl groups are synthesized by copolymerizing uncharged monomers such as styrene with monomers having carboxyl groups, such as acrylic acid". The surfaces of the magnetic particles were modified with carboxyl groups by the method disclosed in Chapter 3.1 "Controlling Dispersion Properties" of "Functionalization of Inorganic Nanoparticles with Organic Molecules", A. Narita and Y. Chujo, Papers Regarding Polymer Molecules, Vol. 65, pp. 321-333, 2008; and "Synthesis of iron oxide nanoparticles under oxidizing environment and their stabilization in aqueous and non-aqueous media", D. Maity and D. C. Agrawal, Journal of Magnetism and Magnetic Materials, Vol. 308, pp. 46-55, 2007.

In FIGS. 4A through 4C and FIGS. 5A through 5C, bright (white) portions are where the particles are displayed.

In FIG. 5A, it can be seen that partial agglomeration occurs among the magnetic particles during the initial dispersion, whereas the magnet enveloping dielectric particles are uniformly dispersed during the initial dispersion, with very little agglomeration.

In FIG. 4B and FIG. 5B, it can be seen that both the magnet enveloping dielectric particles and the magnetic particles are agglomerated and localized along magnetic field lines when the magnetic fields are applied. Note that the magnet enveloping dielectric particles are localized in a more linear manner along the magnetic field lines compared to the magnetic particles.

In FIG. 5C, it is recognized that the magnetic particles are in a state in which they are agglomerated with each other. In contrast, FIG. 4C is bright as a whole and it is difficult to discriminate each particle, but it can be seen that the magnet enveloping dielectric particles are not agglomerated with each other and that redispersion has been initiated.

The dispersion properties of the magnetic particles are lower than the dispersion properties of the magnet enveloping dielectric particles, even in cases that the surfaces of each are modified with functional groups by optimal surface modification methods. This is believed to be caused by the fact that the absolute number of the functional groups which are provided on the surfaces of the magnetic particles as surface modifications is considerably lower that of the magnet enveloping dielectric particles, which results in attraction forces due to magnetization becoming greater than the repelling forces among the particles due to the polarities of the functional groups.

As described above, the magnet enveloping dielectric particles have much higher dispersion properties compared to the magnetic particles. It is considered that even if the magnetic particles within the magnet enveloping dielectric particles are magnetized and the dielectric particles agglomerate due to storage conditions, the magnet enveloping dielectric particles can be dispersed without agglomerating within liquid samples.

The magnet enveloping dielectric particles are employed in the detecting methods of the present invention to be described hereinafter. Therefore, surface modifications are easily administered, and high dispersion properties can be obtained. In addition, when photoresponsive labels are excited during detection of optical signals, metal quenching occurs in cases that the photoresponsive labels are in the vicinities of metal materials due to energy transitions. However, in the magnet enveloping dielectric particles, the magnetic particles are enveloped within the dielectric. Therefore, the magnetic particles and the photoresponsive labels can be separated to a degree, and metal quenching can be suppressed.

[First Embodiment of the Detecting Method]

The detecting method according to a first embodiment of the present invention is a biosensing method that detects whether antigens, which are detection target substances, are present within biological samples (urine, blood, mucous), which are targets of examination, and/or the amounts (concentrations) thereof. FIG. 6 is a schematic diagram that illustrates the configuration of a detecting apparatus 1 for executing the detecting method according to the first embodiment. FIGS. 7A and 7B are diagrams for explaining the steps of the detecting method according to the first embodiment of the present invention.

A sample cell 10 which is employed in the detecting method of the first embodiment has a transparent dielectric plate 11 as its bottom surface, which is a wall of the sample cell 10 having a sample contacting surface that contacts a liquid sample S. A metal film 12 is formed by vapor deposition or the like on the dielectric plate 11 on the side of the sample contacting surface. Note that the region at which the metal film 12 is formed constitutes a sensor portion 14. It is desirable for the thickness of the metal layer 12 to be determined such that surface plasmon is strongly excited, taking the material of the metal layer 12a and the wavelength of the laser beam L0 into consideration. For example, in the case that a laser beam having a central wavelength of 780 nm is employed as an excitation light beam, and an Au film is employed as the metal layer 12, a favorable thickness of the metal layer 12 is 50 nm±20 nm. In this case, it is more preferable for the thickness of the metal layer 12 to be 47 nm±10 nm. Note that it is preferable for the metal layer 12a to be a metal having at least one of Au, Ag, Cu, Al, Pt, Ni, Ti, and alloys thereof as a main component.

Figure 6:
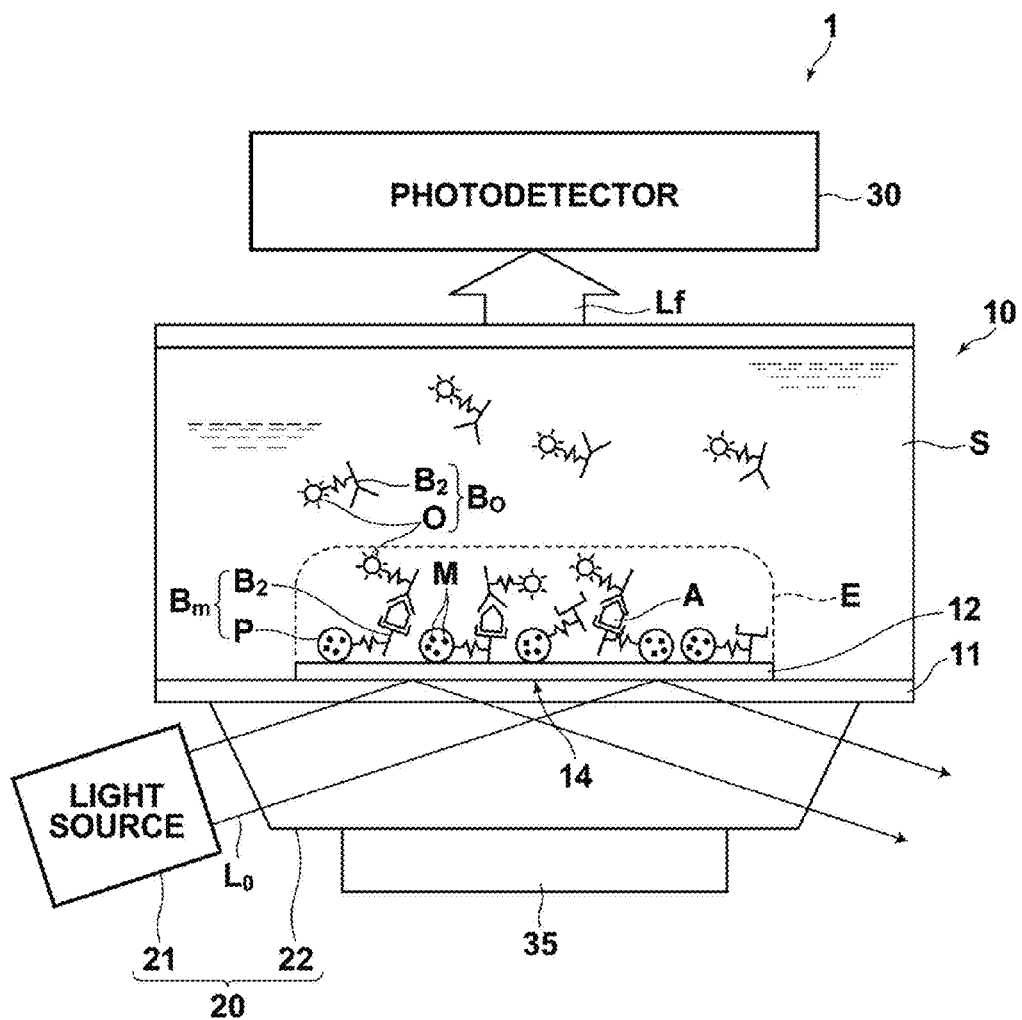
FIG. 6 is a schematic diagram that illustrates the configuration of a detecting apparatus for executing a detecting method according to a first embodiment of the present invention.

The detecting apparatus 1 illustrated in FIG. 6 is equipped with: an excitation light irradiating optical system 20 for irradiating excitation light onto only a predetermined region within the sample cell 10; a photodetector 30 for detecting fluorescence positioned above the sample cell 10; and a magnetic field applying means 35 for applying magnetic fields to draw (agglomerate) sandwich combinations formed within the sample cell 10 to a local region in the vicinity of the metal film 12.

The excitation light irradiating optical system 20 emits a laser beam L0 such that it enters the interface between the dielectric plate 11 and the metal layer 12 through the bottom surface of the dielectric plate 11 at an incident angle that satisfies conditions for total reflection, to generate evanescent light on the metal film 12 as excitation light. A region E into which the evanescent light leaks is within approximately a single wavelength of the laser beam L0 from the interface. This region E corresponds to the predetermined region. The excitation light irradiating optical system 20 is equipped with: the light source 21, constituted by a semiconductor laser (LD), for outputting the laser beam L0; and a prism 22, which is provided such that one of the surfaces thereof is in contact with the dielectric plate 11. The prism 22 guides the laser beam Lo into the dielectric plate 11 such that the laser beam L0 is totally reflected at the interface between the dielectric plate 11 and the metal layer 12. Note that the prism 22 and the dielectric plate 11 may be formed integrally, or may be in contact via refractive index matching oil. The light source 21 is positioned such that the laser beam L0 enters the interface between the dielectric plate and the metal film at a specific angle greater than or equal to a total reflection angle that causes surface plasmon resonance to occur, through the prism 22. The laser beam L0 may be emitted as a fan beam that includes the specific angle. Further, light guiding members may be provided between the light source 21 and the prism 22 as necessary. Note that the laser beam L0 enters the interface as p polarized light, in order to effectively induce the surface plasmon.

Examples of photodetectors that may be employed as the photodetector 30 include: CCD's, PD's (photodiodes), photomultiplier tubes, and c-MOS's.

The magnetic field applying means 35 may be an electromagnet, or a permanent magnet. If an electromagnet is employed, current may be caused to flow through the coils thereof to generate a magnetic field when the magnetic particles are to be drawn into the local region. In the case that a permanent magnet is employed, the magnet may be positioned beneath the sensor portion 14 as illustrated in FIG. 6 when the magnetic particles are to be drawn into the local region. When the magnetic field application is to be ceased, the magnet may be moved to a position at which a magnetic field is no longer generated in the vicinity of the sensor portion 14. Examples of permanent magnets include alnico magnets, ferrite magnets, MK steel, KS steel, samarium cobalt magnets, and neodymium magnets. However, the type of magnet to be employed as the permanent magnet is not particularly limited.

The steps of the biosensing method according to the detecting method of the first embodiment will be described. FIG. 7A and FIG. 7B are schematic diagrams that illustrate the sample cell prior to and following magnetic field application.

In the detecting method of the first embodiment, first, a magnetic property imparted binding substance Bm, which is a first binding substance B1 that specifically binds with a detection target substance A, having magnet enveloping dielectric particles P, which have magnetic particles M enveloped therein and the surfaces of which are modified with functional groups that exhibit polarity within a liquid sample, attached thereto, is prepared. Next, a labeling binding substance B0, which is a second binding substance B2 that specifically binds with the detection target substance A, having photoresponsive labels O attached thereto, is prepared. Here, the first binding substance B1 and the second binding substance are primary antibodies and secondary antibodies that bind with different portions (epitopes) of the detection target substance A, which is an antigen. The amine coupling method that employs the carboxyl groups, which are provided as surface modifications, may be employed to immobilize the antibodies onto the magnet enveloping dielectric particles P.

Fluorescent pigment molecules are employed as the photoresponsive labels O. Note that the photoresponsive labels O of the present invention are not limited to being fluorescent pigment molecules and may be any type of photoresponsive label, as long as it generates optical signals in response to being irradiated by excitation light. Examples of such photoresponsive labels include: those that generate fluorescence in response to being irradiated by excitation light, such as fine fluorescent particles, in which fluorescent pigment molecules are enveloped within transparent materials, and quantum dots; and those that generate scattered light or local plasmon, such as fine metal particles.

Next, the liquid sample S, which is a target of examination, the magnetic property imparted binding substance Bm and the labeling binding substance B0 are mixed to cause binding reactions to occur, as illustrated in FIG. 7A. Note that the timings at which the magnetic property imparted binding substance Bm and the labeling binding substance B0 are mixed into the liquid sample S is not particularly limited. The two may be mixed into the liquid sample S either simultaneously or sequentially. In the case that the antigens A are present within the liquid sample S, sandwich combinations are formed by the magnetic property imparted binding substance Bm (primary antibodies B1), the antigens A, and the labeling binding substance B0 (secondary antibodies B1).

Thereafter, a magnetic field is generated within the sample cell 10 that holds the liquid sample S, into which the magnetic property imparted binding substance Bm and the labeling binding substance B0 have been mixed. The magnetic property imparted binding substance Bm are drawn toward the surface of the metal film 12, which is a local region within the sample cell 10, as illustrated in FIG. 7B. Detection of optical signals is performed in a state in which the magnetic property imparted binding substance Bm are drawn onto the surface of the metal film 12.

When the magnetic property imparted binding substance Bm are drawn into the local region, the antigens A and the labeling binding substance B0 that form sandwich combinations with the magnetic property imparted binding substance Bm are also drawn into a predetermined region that includes the local region as a result. Meanwhile, non reactive labeling binding substance B0 float within the liquid sample without being drawn into the predetermined region. That is, only the labeling binding substance B0 which have reacted with the antigens A are localized within the predetermined region, from among the mixed labeling binding substances.

Therefore, signals can be obtained only from labels that have undergone binding reactions with the antigens, by irradiating excitation light only onto the predetermined region that includes the local region, and causing optical signals to be generated by the photoresponsive labels O which are present within the predetermined region.

The excitation light irradiating optical system 20 causes the laser beam L0 to enter the interface between the dielectric plate 11 and the metal film 12 under conditions of total reflection. When the laser beam L0 is totally reflected at the interface, evanescent light leaks out toward the surface of the metal film 12, and surface plasmon is also generated. The surface plasmon amplifies the evanescent light, and the amplified evanescent light excites the fluorescent pigment molecules, which are the photoresponsive labels O, to generate fluorescence Lf. That is, in the first embodiment, evanescent light is the excitation light that excites the fluorescent pigment molecules, which are the photoresponsive labels, and the region E including the surface of the metal film 12, into which the evanescent light leaks, is the predetermined region.

The photodetector 30 detects the fluorescence Lf. The intensity of the fluorescence Lf is also amplified by the electric field enhancing effect of surface plasmon resonance. Therefore signals having a favorable S/N ratio can be obtained.

The amount of the detection target substance is derived on the amount of detected fluorescence Lf. The amount (concentration) of the detection target substance may be derived based on a standard curve that represents the relationship between detected amounts of fluorescence and concentrations. Note that here, deriving the amount of the detection target substance includes determining whether the detection target substance is present.

The detecting method of the first embodiment performs binding reactions within the liquid phase. Therefore, the reaction speed is faster compared to a case in which binding reactions include binding with a solid phase. In addition, the reaction speed is further improved because the dispersion properties of the particles are superior. By employing the magnet enveloping dielectric particles to effectively draw the sandwich combinations to the sensor portion, the labeling binding substances that have reacted with the antigens, which are detection target substances, can be easily separated from non reactive labeling binding substances. By employing the magnet enveloping dielectric particles having particle sizes of 100 nm or greater to form sandwich combinations of 200 nm or greater, the concentration speed (the speed at which the combinations are localized into the local region) during magnetic field application can be of a level suited for practical use. Further, when photoresponsive labels are excited during detection of optical signals, metal quenching occurs in cases that the photoresponsive labels are in the vicinities of metal materials due to energy transitions. However, in the magnet enveloping dielectric particles, the magnetic particles are enveloped within the dielectric. Therefore, the magnetic particles and the photoresponsive labels can be separated to a degree, and metal quenching can be suppressed. Thereby, the S/N ratio of the optical signals can be improved, and fluctuations in the signal amounts can be suppressed.

Note that in the first embodiment, the S/N ratio is improved by providing the metal film 12 on the dielectric plate 11 to utilize the electric field enhancing effect of surface plasmon resonance. However, the detecting method of the present invention may be applied to evanescent fluorometry that does not employ the metal film 12, and the aforementioned advantageous effects can be obtained by employing the magnet enveloping dielectric particles.

[Second Embodiment of the Detecting Method]

Figure 8:
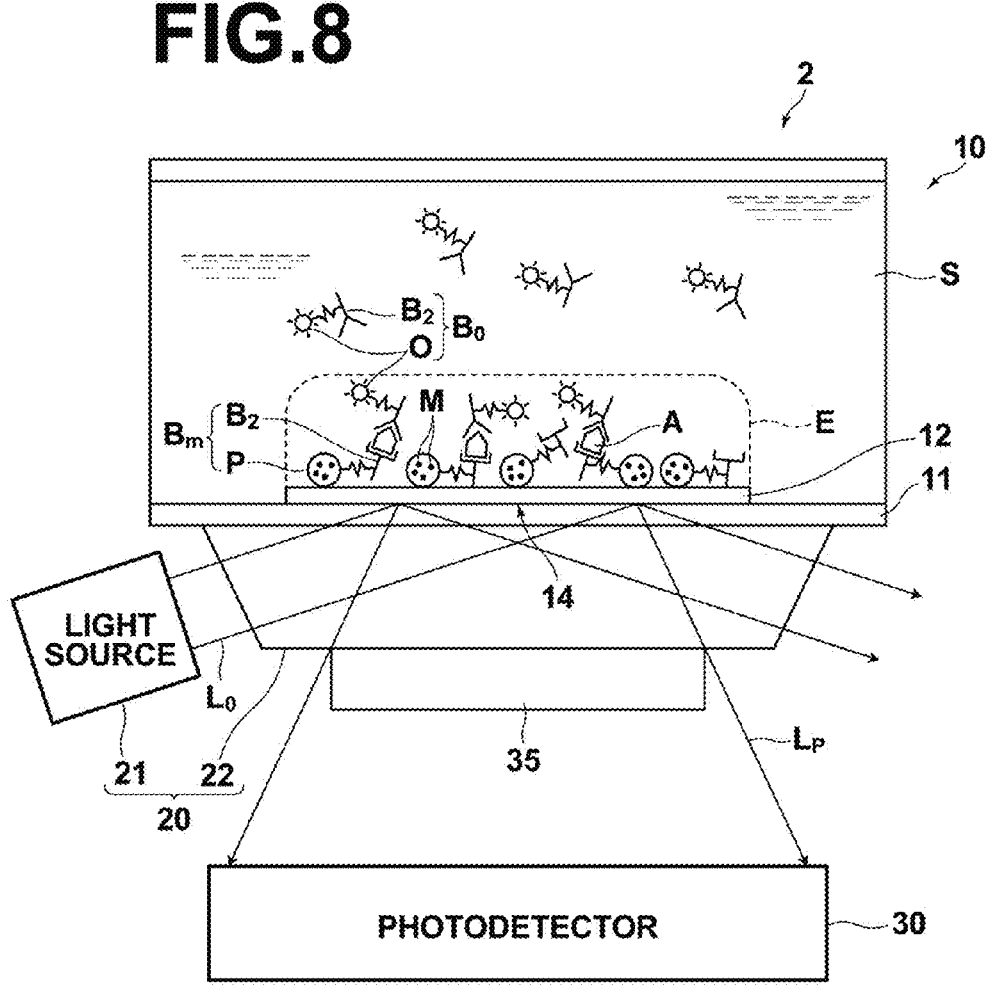
FIG. 8 is a schematic diagram that illustrates the configuration of a detecting apparatus for executing a detecting method according to a second embodiment of the present invention.

A detecting method according to a second embodiment of the present invention and a detecting apparatus 2 for executing the detecting method will be described with reference to FIG. 8. In the following description, structural elements which are the same as those of the first embodiment will be denoted with the same reference numerals, and detailed descriptions thereof will be omitted. The detecting apparatus 2 differs from the apparatus 1 of the first embodiment in the placement of the photodetector 30 and the method by which the optical signals are detected.

In the second embodiment, the photodetector 30 is positioned beneath the sensor portion 14 of the sample cell 10 so as to detect radiant light Lp, which is radiated toward the side of the dielectric plate 11 opposite the side on which the metal film is formed, from surface plasmon which is newly excited at the metal film by fluorescence generated by the fluorescent labels due to excitation.

The steps of sensing according to the detecting method of the second embodiment are the same as those of the first embodiment. The second embodiment differs from the first embodiment in that radiant light Lp, which is generated due to fluorescence newly exciting surface plasmon at the surface of the metal film 12, is detected as the optical signals instead of directly detecting fluorescence, which is the optical signals from the photoresponsive labels O.

In the second embodiment, the liquid sample S, the magnetic property imparted binding substance Bm, and the labeling binding substance B0 are mixed within the sample cell 10 to form sandwich combinations by binding reactions. Thereafter, the magnet 35 is positioned beneath the dielectric plate 11 to draw the sandwich combinations toward the sensor portion 14. The laser beam L0 is emitted by the excitation light irradiating optical system 20 while the sandwich combinations are drawn to the sensor portion 14, in the same manner as in the first embodiment.

The laser beam L0 is irradiated by the excitation light irradiating optical system 20 toward the interface between the dielectric plate 11 and the metal film 12 such that conditions for total reflection are satisfied. When the laser beam L0 is totally reflected at the interface, evanescent light leaks into the sample S on the metal film 12, and surface plasmon is generated. The surface plasmon amplifies the evanescent light, and the amplified evanescent light excites the fluorescent pigment molecules, which are the photoresponsive labels O, to generate fluorescence Lf. The fluorescence Lf is amplified by the surface plasmon, and newly generates surface plasmon on the surface of the metal film 12. Thereby, radiant light Lp caused by the surface plasmon is radiated at a specific angle toward the underside of the dielectric plate 11. The presence and/or the amount of the detection target substance A, which is bound to the fluorescent label binding substance BF, is detected by detecting the radiant light Lp with the photodetector 30.

The radiant light Lp is generated when the fluorescence Lf couples with surface plasmon of a specific wave number at the metal layer 12. The wavelength of the fluorescence Lf determines the wave number at which the coupling with the surface plasmon occurs. Therefore, the radiant angle of the radiant light Lp is determined according to the wave number. Generally, the wavelength of the laser beam L0 and the wavelength of the fluorescence Lf are different. Therefore, wave number of the surface plasmon which is excited by the fluorescence Lf is different from the wave number of the surface plasmon which is excited by the laser beam L0, and accordingly, the radiant light Lp is radiated at an angle different from the incident angle of the laser beam L0.

In the second embodiment as well, the assay is performed employing the magnetic property imparted binding substance Bm constituted by the magnet enveloping dielectric particles P and the first binding substance B1, and fluorescence is caused to be generated while the magnet enveloping dielectric particles P are drawn toward the sensor portion by the magnetic field applying means, such as a magnet. Radiant light, which is generated by the amplified fluorescence, is detected. Accordingly, the same advantageous effects as those obtained by the first embodiment can be obtained.

Further, the second embodiment detects the light generated due to fluorescence generated at the surface of the sensor from the rear side of the sensor. Therefore, the distance that the fluorescence Lf travels through media that absorbs light can be reduced to several 10's of nanometers. Accordingly, light absorption by blood, for example, becomes negligible, and measurement becomes possible without performing preliminary processes of removing coloring components such as red blood cells from blood with a centrifuge, or passing blood through blood cell filters to obtain blood serum or plasma.

[Third Embodiment of the Detecting Method]

Figure 9:
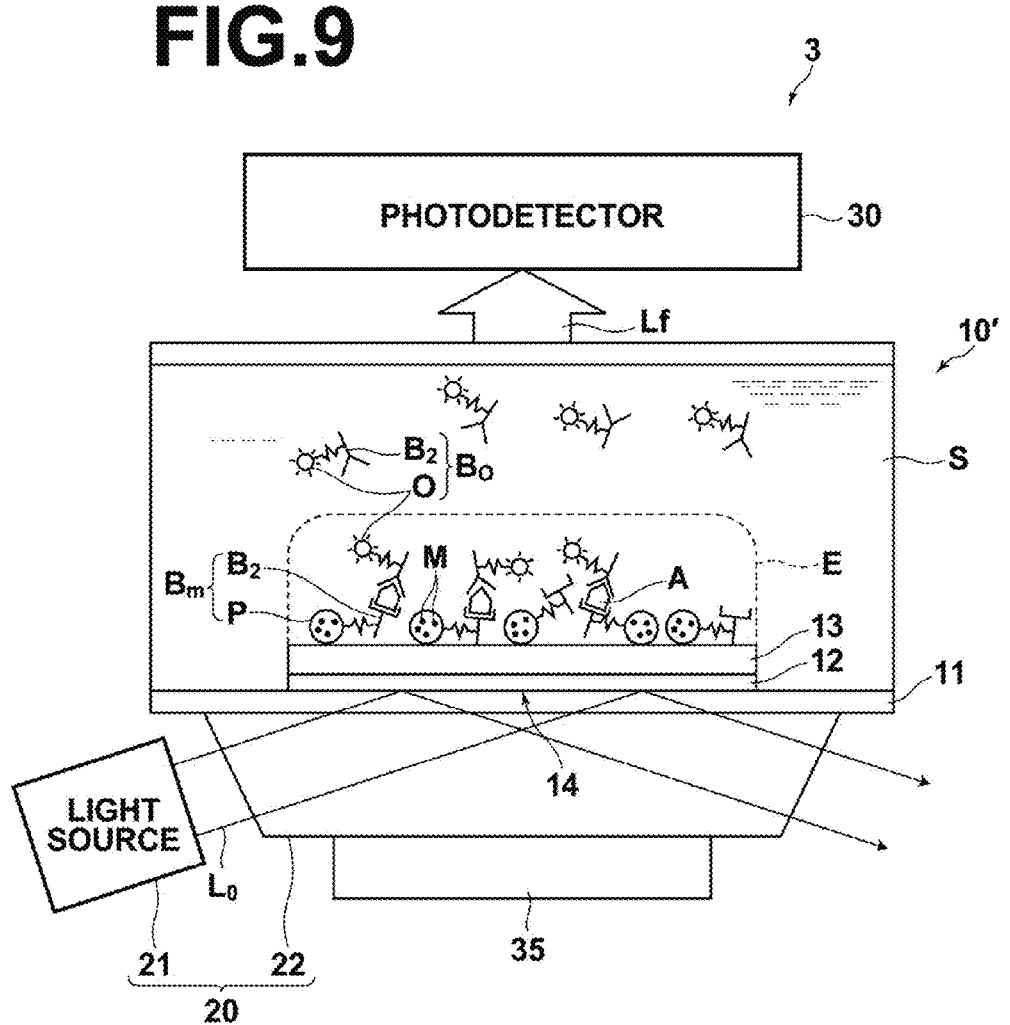
FIG. 9 is a schematic diagram that illustrates the configuration of a detecting apparatus for executing a detecting method according to a third embodiment of the present invention.

A detecting method according to a third embodiment of the present invention and a detecting apparatus 3 for executing the detecting method will be described with reference to FIG. 9. The configuration of the detecting apparatus 3 of the third embodiment is the same as that of the apparatus 1 of the first embodiment. However, a sample cell 10' which is employed in the third embodiment differs from the sample cell 10 of the first and second embodiments in that the sensor portion 14 is further equipped with an optical waveguide layer 13 provided on the surface of the metal film 12.

The steps of sensing according to the detecting method of the third embodiment are the same as those of the first and second embodiments. The third embodiment differs from the first and second embodiments the principle of electric field enhancement on the sensor portion 14.

In the third embodiment, the laser beam L0 is emitted by the excitation light irradiating optical system 20 such that it enters the interface between the dielectric plate and the metal film under conditions of total reflection. When the laser beam L0 enters the interface under conditions of total reflection, evanescent light is generated on the sensor portion 14 as excitation light, in the same manner as in the first and second embodiments. The evanescent light excites an optical waveguide mode of the optical waveguide layer 13, to amplify the evanescent light that leaks onto the surface of the optical waveguide layer 13. The third embodiment differs from the first embodiment in that the evanescent light is amplified by excitation of the optical waveguide mode.

The thickness of the optical waveguide layer 13 is not particularly limited, and may be determined such that the optical waveguide mode is induced, taking the wavelength and incident angle of the laser beam L0 and the refractive index of the optical waveguide layer 13 into consideration. For example, in the case that a laser beam having a central wavelength of 780 nm is employed as the laser beam L0 and a single layer of silicon oxide film is employed as the optical waveguide layer 13, it is preferable for the thickness of the optical waveguide layer 13 to be within a range from 500 nm to 600 nm. The optical waveguide layer 13 may be of a laminated structure that includes at least one internal optical waveguide layer constituted by optical waveguiding material. It is preferable for the laminated structure to be of an alternating laminated structure, in which the internal optical waveguide layer and an internal metal layer are alternately provided in this order from the side of the metal film.

Note that the fluorescence emitted by the fluorescent pigment molecules is also enhanced by the electric field enhancing effect of the optical waveguide mode. The presence and/or the amount of the detection target substance, which is bound to the labeling binding substance BF, is detected by detecting the fluorescence with the photodetector 30.

In the second embodiment as well, the assay is performed employing the magnetic property imparted binding substance Bm constituted by the magnet enveloping dielectric particles P and the first binding substance B1, and fluorescence is detected while the magnet enveloping dielectric particles P are drawn toward the sensor portion by the magnetic field applying means, such as a magnet. Accordingly, the same advantageous effects as those obtained by the first embodiment can be obtained.

Note that the sample cell 10' equipped with the optical waveguide layer 13 may be configured such that radiant light is detected from beneath the sensor portion 14 as in the detecting method of the second embodiment. In this case, the fluorescence, which is the optical signals emitted by the fluorescent pigment molecules that function as the photoresponsive labels, newly excites an optical waveguide mode in the optical waveguide layer, and the optical signals are indirectly detected by detecting radiant light that accompanies excitation of the optical waveguide mode.

As described in each of the above embodiments, the detecting method of the present invention detects optical signals which are generated by photoresponsive labels within a predetermined region being excited. The optical signals (fluorescence in the above embodiments) generated by the photoresponsive labels may be directly detected or indirectly detected.

In each of the above embodiments, sensing methods that employ assays according to the non competitive sandwich method has been described. However, the detecting method of the present invention may be applied not only to the sandwich method, but also to sensing methods that employ assays according to the competition method. In the case that assays are performed according to the competition method, a third binding substance that specifically bind with the first binding substance (primary antibody) in competition with the detection target substance A, having photoresponsive labels attached thereto, may be employed as the labeling binding substance.

In addition, each of the embodiments described above employed fluorescent pigment molecules as the photoresponsive labels. Fine metal particles are another preferred example of the photoresponsive labels. The fine metal particles which are to be utilized as labels may be fine particles having at least the surfaces thereof covered by a metal film, and of a particle size that causes local plasmon to be generated when irradiated by light. The shape of the fine metal particles is not particularly limited, and examples of possible shapes include spheres and rods. Fine metal particles scatter evanescent light to generate scattered light, which may be detected as optical signals. Alternatively, in the case that a material having at least one metal selected from a group consisting of gold (Au), silver (Ag), copper (Cu), aluminum (Al), platinum (Pt), nickel (Ni), titanium (Ti), and alloys thereof as the main component thereof is employed as the material of the fine metal particles (or the material of the metal film on the surfaces of particles), local plasmon is generated on the surfaces of the fine metal particles when irradiated by excitation light. A configuration may be adopted, wherein the local plasmon functions as optical signals that excite surface plasmon on the metal film, or excite an optical waveguide mode in the optical waveguide layer, and radiant light that accompanies such excitation is detected. Note that in this case, it is preferable for the particle size of the fine metal particles to be smaller than the wavelength of the excitation light, to enable effective excitation of local plasmon.

The optical system that causes evanescent light to be generated as described in the above embodiments is commonly used as the excitation light irradiating optical system that irradiates light only onto the predetermined region. However, in the case that polymers that emit fluorescence when excited by two photon absorption are employed as the photoresponsive labels, light having an extremely high energy level must be irradiated to cause two photon absorption excitation to occur. In this case, an excitation light irradiating optical system, in which a laser beam is converged in the predetermined region where sandwich combinations are localized by an objective lens having a large NA, such that the laser beam functions as excitation light that causes two photon absorption excitation to occur only within the predetermined region, may be employed.

What is claimed is:

1. A detecting method comprising the steps of:
preparing a magnetic property imparted binding substance, which is a first binding substance that specifically binds with a detection target substance, having magnet enveloping dielectric particles, which have magnetic particles enveloped therein and the surfaces of which are modified with functional groups that exhibit polarity within a liquid sample, attached thereto;
preparing a labeling binding substance, which is one of a second binding substance that specifically binds with the detection target substance and a third binding substance that specifically binds with the first binding substance in competition with the detection target substance, having photoresponsive labels attached thereto;
mixing the liquid sample, which is a target of inspection, the magnetic property imparted binding substance, and the labeling binding substance, to cause binding reactions to occur;
generating a magnetic field within a sample cell that contains the liquid sample, in which the magnetic property imparted binding substance and the labeling binding substance are mixed, to draw the magnetic property imparted binding substance to a local region within the sample cell;
irradiating excitation light only onto a predetermined region that includes the local region, in a state in which the magnetic property imparted binding substance is drawn to the local region, to cause optical signals to be generated by the photoresponsive labels which are present within the predetermined region;
detecting the optical signals; and
determining the amount of the detection target substance within the liquid sample, based on the amount of detected optical signals, wherein:
the maximum length of the combinations of the magnetic property imparted binding substance, the detection target substance, and the labeling binding substance, which is the second binding substance having the photoresponsive labels attached thereto, is greater than or equal to 200 nm.

2. A detecting method as defined in claim 1, wherein:
the particle size of the magnet enveloping dielectric particles is within a range from 100 nm to 1 μm.

3. A detecting method as defined in claim 1, wherein:
one of an iron based magnetic material and a platinum based magnetic material is employed as the magnetic particles; and
infrared radiation is employed as the excitation light.

4. A detecting method as defined in claim 1, wherein:
a sample cell with a portion of a wall having a sample contacting surface that contacts the liquid sample, which is constituted by a transparent dielectric plate, is employed as the sample cell;
the vicinity of the sample contacting surface is employed as the local region;
light is irradiated onto the sample contacting surface of the of the dielectric plate from outside the wall constituted by the dielectric plate under conditions of total reflection, such that evanescent light is generated at the sample contacting surface; and
the evanescent light is employed as the excitation light.

5. A detecting method as defined in claim 4, wherein:
a sample cell, in which a metal film is formed on the sample contacting surface of the dielectric plate, is employed as the sample cell.

6. A detecting method as defined in claim 5, wherein:
a sample cell, which is equipped with an optical waveguide layer provided on the metal film, is employed as the sample cell.

7. A detecting method as defined in claim 5, wherein:
the optical signals generated by the photoresponsive labels due to the irradiation of the excitation light are indirectly detected, by detecting radiant light that radiates due to excitation of surface plasmon at the metal film by the optical signals.

8. A detecting method as defined in claim 6, wherein:
the optical signals generated by the photoresponsive labels due to the irradiation of the excitation light are indirectly detected, by detecting radiant light that radiates due to excitation of an optical waveguide mode of the optical waveguide layer by the optical signals.

9. A detecting method as defined in claim 1, wherein:
the optical signals generated by the photoresponsive labels due to the irradiation of the excitation light are directly detected.

10. Magnet enveloping dielectric particles to be employed in the detecting method defined in claim 1, comprising:
magnetic particles enveloped therein; and
functional groups that exhibit polarity within liquid samples, provided as surface modifications.

11. Magnet enveloping dielectric particles as defined in claim 10, wherein:
the functional groups are carboxyl groups.

12. Magnet enveloping dielectric particles as defined in claim 10, wherein:
the particle size is within a range from 100 nm to 1 μm.

13. Magnet enveloping dielectric particles as defined in claim 10, wherein:
one of an iron based magnetic material and a platinum based magnetic material is employed as the magnetic particles.

14. A detecting method comprising the steps of:
preparing a magnetic property imparted binding substance, which is a first binding substance that specifically binds with a detection target substance, having magnet enveloping dielectric particles, which have magnetic particles enveloped therein and the surfaces of which are modified with functional groups that exhibit polarity within a liquid sample, attached thereto;
preparing a labeling binding substance, which is one of a second binding substance that specifically binds with the detection target substance and a third binding substance that specifically binds with the first binding substance in competition with the detection target substance, having photoresponsive labels attached thereto;

mixing the liquid sample, which is a target of inspection, the magnetic property imparted binding substance, and the labeling binding substance, to cause binding reactions to occur;

generating a magnetic field within a sample cell that contains the liquid sample, in which the magnetic property imparted binding substance and the labeling binding substance are mixed, to draw the magnetic property imparted binding substance to a local region within the sample cell;

irradiating excitation light only onto a predetermined region that includes the local region, in a state in which the magnetic property imparted binding substance is drawn to the local region, to cause optical signals to be generated by the photoresponsive labels which are present within the predetermined region;

detecting the optical signals; and determining the amount of the detection target substance within the liquid sample, based on the amount of detected optical signals, wherein:

the maximum length of the combinations of the magnetic property imparted binding substance and the labeling binding substance, which is the third binding substance having the photoresponsive labels attached thereto, is greater than or equal to 200 nm.

15. A detecting method as defined in claim 14, wherein:
the particle size of the magnet enveloping dielectric particles is within a range from 100 nm to 1 µm.

16. A detecting method as defined in claim 14, wherein:
one of an iron based magnetic material and a platinum based magnetic material is employed as the magnetic particles; and
infrared radiation is employed as the excitation light.

17. A detecting method as defined in claim 14, wherein:
a sample cell with a portion of a wall having a sample contacting surface that contacts the liquid sample, which is constituted by a transparent dielectric plate, is employed as the sample cell;
the vicinity of the sample contacting surface is employed as the local region;
light is irradiated onto the sample contacting surface of the of the dielectric plate from outside the wall constituted by the dielectric plate under conditions of total reflection, such that evanescent light is generated at the sample contacting surface; and
the evanescent light is employed as the excitation light.

18. A detecting method as defined in claim 14, wherein:
the optical signals generated by the photoresponsive labels due to the irradiation of the excitation light are directly detected.

* * * * *